(12) United States Patent
Fanta et al.

(10) Patent No.: US 6,669,962 B2
(45) Date of Patent: Dec. 30, 2003

(54) STARCH MICROCAPSULES FOR DELIVERY OF ACTIVE AGENTS

(75) Inventors: George F. Fanta, Morton, IL (US); Clarence A. Knutson, Peoria, IL (US); Kenneth Eskins, Laura, IL (US); Frederick C. Felker, Morton, IL (US)

(73) Assignee: The United States of America as represented by The Secretary of Agriculture, Washington, DC (US)

( * ) Notice: Subject to any disclaimer, the term of this patent is extended or adjusted under 35 U.S.C. 154(b) by 22 days.

(21) Appl. No.: 09/745,043

(22) Filed: Dec. 20, 2000

(65) Prior Publication Data

US 2001/0006698 A1 Jul. 5, 2001

Related U.S. Application Data

(63) Continuation of application No. 09/135,999, filed on Aug. 18, 1998, now Pat. No. 6,238,677.

(51) Int. Cl.[7] .............................. A61K 9/14; A61K 9/16
(52) U.S. Cl. ........................ 424/490; 424/489; 424/491; 424/493
(58) Field of Search ................. 424/489, 490, 424/491, 493; 426/4, 122

(56) References Cited

U.S. PATENT DOCUMENTS

| | | | | |
|---|---|---|---|---|
| 4,749,800 A | * | 6/1988 | Jobe et al. ................... | 549/452 |
| 4,789,550 A | * | 12/1988 | Hommel et al. ............. | 424/493 |
| 4,806,355 A | * | 2/1989 | Goosen et al. ............... | 424/424 |
| 5,055,429 A | * | 10/1991 | James et al. .................. | 501/80 |
| 5,348,803 A | * | 9/1994 | Schlaemus et al. ....... | 428/402.2 |
| 5,354,556 A | * | 10/1994 | Sparks et al. ................ | 424/419 |
| 5,676,994 A | * | 10/1997 | Eskins et al. ................ | 426/602 |
| 5,846,530 A | * | 12/1998 | Soon-Shiong et al. ..... | 424/93.7 |
| 6,200,548 B1 | * | 3/2001 | Bichon et al. ............. | 424/9.51 |

FOREIGN PATENT DOCUMENTS

EP  0 470 872  * 12/1992

* cited by examiner

Primary Examiner—Thurman K. Page
Assistant Examiner—S. Tran
(74) Attorney, Agent, or Firm—John D. Fado; Curtis P. Ribando

(57) ABSTRACT

Polysaccharide-based shells are provided having use for forming water-dispersible microcapsular delivery systems for both hydrophilic and lipophilic drugs, pharmaceuticals, cosmetics and other active agents. These shells are prepared by intimately blending a solubilized polysaccharide with a lipophilic material to produce spherical droplets of the lipophilic material coated with the polysaccharide, diluting the emulsion with a solvent, and isolating the polysaccharide shells from the diluted emulsion.

19 Claims, 1 Drawing Sheet

STARCH MICROCAPSULES FOR DELIVERY OF ACTIVE AGENTS

This application is a cont of Ser. No. 09/135,999 filed Aug. 18, 1998, is now U.S. Pat. No. 6,238,677

BACKGROUND OF THE INVENTION

1. Field of the Invention

This invention relates to microscopic-sized starch-based shells (microspheres) and their use in forming microcapsules having utility as delivery systems for drugs, pharmaceuticals, cosmetics and other active agents. These microcapsules (coated droplets) are dispersible in an aqueous carrier and can be used in the preparation of aqueous-based delivery systems of active agents that are lipophilic and water-insoluble in nature. The resultant delivery systems are particularly useful for administration of active agents by injection.

2. Description of the Prior Art

In a three part series of articles discussing the manufacturing techniques for producing microspheres and microcapsules, Arshady [Polymer Eng. & Sci. 29:1746–1758 (1989); and Polymer Eng. & Sci. 30:905–924 (1990)] describes three principal techniques in current practice: (1) suspension cross-linking; (2) coacervation; and (3) solvent evaporation. In suspension cross-linking, a stable droplet suspension of a polymer solution (or melt) is produced in an immiscible liquid, and the droplets are gradually hardened by covalent cross-linking. This process may involve cross-linking of polysaccharides, proteins, or synthetic polymers. Coacervation involves macromolecular aggregation (or phase separation) brought about by partial desolvation of fully solvated macromolecules. Gelatin, gum arabic, and ethylcellulose are commonly used in this process. The solvent extraction/solvent evaporation processes involve droplet formation followed by solvent removal. The extraction or evaporation of the solvent is accompanied by a corresponding decrease in the volume and increase in the viscosity of the individual droplets. Various polysaccharides, polysaccharide derivatives, and synthetic polymers can be used in this technique.

Use of starch as a vehicle for the delivery of drugs and pharmaceuticals is currently limited to only a few specific areas, for example: (1) use of powdered starch (or starch derivatives) in the formulation and pressing of tablets, which are then ingested to deliver their active ingredient; (2) use of capsules that are prepared by molding starch in the presence of plasticizing agents such as water. Capsules are then filled with active ingredient in a separate step. These capsules are thick-walled, have large diameters and also must be ingested to deliver their active ingredient. Neither of these two technologies can be used to deliver drugs or pharmaceuticals by injection.

U.S. Pat. No. 5,676,994, which is incorporated herein by reference, describes compositions prepared by mixing starch, water and a lipophilic component at room temperature and then passing this mixture through an excess steam jet cooker. The resulting jet cooked compositions are stable with respect to separation and coagulation of oil droplets and are comprised of microscopic droplets of oil, about 1–10 microns in diameter, uniformly distributed in the starch-water phase. No emulsifying agents, dispersing agents or surface-active agents are used in the process. The amount of oil in the formulation generally does not exceed 65 parts per 100 parts of starch by weight (about 40% of the total product), and preferred compositions are comprised of about 20–40 parts of oil per 100 parts of starch (17–29%, by weight). The one embodiment that produced a composite containing as much as 90% oil was prepared from a starch-soy protein mixture, rather than pure starch (Example 38 in U.S. Pat. No. 5,676,994). The resulting jet cooked dispersions are useful for a number of end-use applications and are characterized by the following properties: (1) they do not phase separate into their oil and water components on prolonged standing; (2) when cooled, they form soft gels that can be easily converted back to pourable fluids by the application of heat; (3) they may be dried, for example by drum drying, to yield solid compositions that are not oily to the touch; and (4) dried compositions hydrate rapidly and are easily redispersed in water to form smooth, stable, lump-free dispersions that are similar in properties and appearance to aqueous compositions that have never been dried. The electron micrographs in a publication by Eskins et al. (*Carbohydrate Polymers*, 29:233–239, 1996) show what appears to be a boundary layer of unknown composition surrounding the lipophilic droplets prepared by the same method as the aforementioned patent. The nature of that boundary layer has not heretofore been characterized.

SUMMARY OF THE INVENTION

We have now discovered a method for making microscopic-sized polysaccharide-based shells having use for forming water-dispersible microcapsular delivery systems for both hydrophilic and lipophilic drugs, pharmaceuticals, cosmetics and other active agents.

This invention is based on the discovery that when a completely solubilized natural polysaccharide and a water-immiscible material are intimately combined under high shear conditions, it is possible to isolate discrete polysaccharide-coated lipophilic droplets without the use of cross-linking agents. These droplets are conveniently separated from the predominantly-polysaccharide fraction of the jet-cooked dispersion by diluting the dispersion with water and then either centrifuging the diluted dispersion or allowing it to stand for a period of time sufficient for the layers to separate under the force of gravity according to their relative densities. Polysaccharide-coated lipophilic droplets are then isolated from either the surface of the dispersion or from the denser layer that settles to the bottom. The isolated droplets may be further purified by washing with water. The polysaccharide coating that surrounds each droplet is stable and prevents the droplets from coalescing when they are isolated, washed, and used for various end-use applications. The polysaccharide coating also causes these droplets to disperse instantly with minimum agitation when they are diluted with water. Moreover, if a volatile lipophilic material is used, hollow spheres can be recovered by permitting the lipophile to evaporate.

In accordance with this discovery, it is an object of this invention to provide new and novel compositions of matter comprised of microscopic-sized, fully biodegradable, natural polysaccharide-based shells useful as microcapsular delivery systems.

It is also an object of the invention to provide micron-sized lipophilic droplets, each droplet being coated with a thin layer of polysaccharide.

Another object of this invention to provide a process for the preparation of the aforementioned lipophile/polysaccharide compositions.

A further object of the invention is to provide injectable drugs and pharmaceuticals comprising aqueous dispersions of the aforementioned microcapsular delivery systems comprising polysaccharide-based shells containing hydrophilic or lipophilic active agents.

Other objects and advantages of the invention will become apparent from the following discussion.

BRIEF DESCRIPTION OF THE DRAWING

Scanning electron micrographs (SEM's) in FIGS. 1–4 were obtained by isolating starch-coated soybean oil droplets from dispersion surfaces, washing the coated droplets with water, and adding small quantities of water-washed product to excess ethanol in order to dehydrate the starch coating and dissolve the soybean oil. The precipitated solid was then critical point dried and examined by SEM using standard procedures.

DETAILED DESCRIPTION OF THE INVENTION

Figure 1:
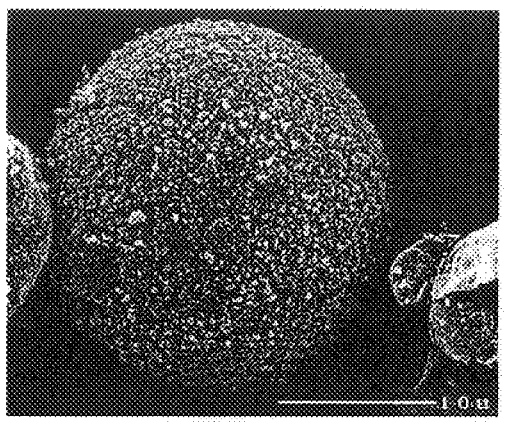
FIG. 1 is a SEM showing an intact starch shell isolated from a product obtained by steam jet cooking normal, food grade cornstarch (having an amylose content of about 25%) with soybean oil in a starch-to-soybean oil weight ratio of 100:40. Coated droplets (shells) were isolated by the "hot-dilution" technique.

The preferred polysaccharide for use in the invention is starch. Starch is a high molecular weight polymer composed of repeating 1,4-alpha-D-glucopyranosyl units (anhydroglucose units or AGU) and is typically a mixture of linear and branched components. The linear component, amylose, has a molecular weight of several hundred thousand; while the molecular weight of the branched amylopectin is on the order of several million. Although normal cornstarch contains about 25% amylose, cornstarch varieties are available commercially that range in amylose content from 0% (waxy cornstarch) to about 70% (high-amylose cornstarch).

Starch is isolated from the seeds and tubers of living plants as granules that typically range from about 5 to 40 microns in diameter, depending upon the plant source. It is well known that starch, as isolated in its native state, is insoluble in water at room temperature. When a water suspension of granular starch is heated, granules slowly take up water with limited swelling. Then, at a definite temperature (typically about 65–70° C.) the granules swell rapidly and irreversibly, as areas of crystallinity within the granule are lost, and hydrogen bonds are broken. The temperature at which this phenomenon occurs is commonly referred to as the gelatinization temperature.

Near the gelatinization temperature, a measurable percentage of the starch, in particular the amylose component, becomes soluble and diffuses out of the granule matrix and into the surrounding water. At temperatures greater than about 70° C., a greater percentage of the starch becomes soluble, and granules become highly swollen and partially disrupted. At temperatures of about 90–100° C., a viscous dispersion of starch in water is obtained. However, despite this outward appearance of solubility, starch is only partially water soluble and exists largely as highly swollen granules and granule fragments that are easily separable from starch solution, for example, by centrifugation. When cornstarch is heated in water to about 95° C., only about 25% of the starch actually dissolves, the remainder being present as swollen granules and granule fragments.

The compositions of this invention are preferably prepared from unmodified starches obtained from cereal grains, such as corn, wheat and rice, or from root crops, such as potato and tapioca. Modified starches may also be used to obtain certain properties not obtainable with unmodified starches. An unmodified starch is one that has not been altered by chemical treatment or reduced in molecular weight by reaction with acids or enzymes. Use of unmodified starches for the preparation of compositions for injection or ingestion into the human body is preferred over modified starches; because unmodified starches have never been treated with potentially toxic chemicals.

Although any available starch variety is suitable for the preparation of these compositions, it is well known that differences in branching and molecular weight can cause differences in starch properties, which can lead to differences in the thickness, rigidity, water solubility and water swellability of the starch layers that surround the lipophilic droplets.

Starches having amylose and amylopectin components in various proportions may be used. Examples of these are waxy cornstarch having an amylose content of essentially 0%, normal cornstarch having an amylose content of approximately 25% and high amylose cornstarch varieties having amylose contents greater than 25%. Mixtures of these various starches can also be used. Since the ratio of amylose to amylopectin determines the rheology and gelling properties of starch solutions as well as the physical properties of the resulting dispersions and gels, the ratio of amylose to amylopectin will be a major factor in determining the thickness and physical properties of the starch coating. Although starch is preferably used in the preparation of these compositions, one may also use cereal flour, which is comprised largely of starch, but also contains the protein components of the cereal grain.

Examples of other natural polysaccharides for use herein include dextran, cellulose, and hydrocolloid gums of plant or microbial origin that have an inherent solubility, or can be physically altered to have a solubility, approximating that of the sheared starches described, below. Such gums include guar, locust bean, and xanthan. Of course, various mixtures of starch and these polysaccharides can also be used. The ensuing discussion will principally make reference to starch as the polysaccharide, with the understanding that aforementioned alternative polysaccharides could replace or be blended with the starch.

As previously stated, the shells of this invention consist essentially of non-cross-linked polysaccharide. This means that the structural component, or backbone, of the shell, that is the material constituting the rigid sphere, forms without the use of cross-linking agents. The term "cross-linking agent" is used herein in its usual sense to refer to any relatively short chain reactive chemical agent useful for covalently bonding polysaccharide molecules to one another. However, it is contemplated that groups, such as mannose or other sugars can be appended from the polysaccharide molecule for the purpose of targeting drugs as described in further detail, below.

The terms "water-immiscible material" and "lipophilic material" are used herein synonymously. In their broadest definitions, these terms are intended to encompass any organic compound that is largely insoluble in water, such as lipids, fats, oils, resins, rosins, silicones, and long chain ethers, alcohols, aldehydes, ketones, carboxylic acids, aliphatic and aromatic hydrocarbons, organic amines, organic polymers, and the like.

Although any lipid, fat, oil or substantially water-insoluble organic compound may be used for the preparation of the compositions of this invention, the particular lipophilic material used will depend upon the end-use application for the final product. For example, compositions prepared for the delivery of drugs and pharmaceuticals will contain bioactive ingredients, either by themselves or dissolved or dispersed within a second lipophilic phase, such as vegetable oil or vitamin E.

Lipophilic materials and/or other active ingredients that are either volatile or that might decompose under the high temperatures of the jet cooking process may be added with high-shear mixing to a jet cooked solution of starch. Jet cooking starch with a heat-stable lipophile prior to addition of the bioactive ingredient facilitates the incorporation of the bioactive component into the formulation. The jet cooked dispersion may also be dried (for example, by drum-drying) and the dried product later redispersed in water, just prior to addition of the bioactive ingredient. In this embodiment of the invention, the active component must be added while the starch dispersion is in a non-retrograded form. It is also essential that the active component be blended into the dispersion under conditions of high shear and turbulence, commensurate with that occurring within the jet cooker itself. On a laboratory scale, a Waring® blender provides sufficient mechanical shear to provide the intimate mixing needed. It is envisioned that a colloid mill could also be used for this purpose. We have discovered that starch can be locked into a non-retrograded form by drying the hot starch-containing dispersion shortly after it exits the steam jet cooker (for example, by drum drying). It is then possible to redisperse the dried product in water and introduce the active ingredient under high-shear conditions to form a final dispersion comparable to that produced by co-jet cooking.

Compositions of the invention are prepared by initially combining starch and lipophilic material in amounts ranging from about 5 parts to about 900 parts of lipophile, by weight, per 100 parts of starch (about 5–90% of the combined starch/lipophilic material composition on a dry weight basis). The upper practical limit for the lipophilic material content of the final composite composition is usually dictated by the point at which the lipophilic material begins to separate from the recovered product. For most embodiments envisioned herein, the upper limit of lipophilic material would not exceed 65 parts lipophilic material per 100 parts by weight of the starch (40%). Preferred compositions are comprised of about 20 parts to 50 parts of lipophilic material per 100 parts by weight of starch (17–33%).

The usual and most common method for preparing the compositions of this invention is to first prepare a blend of starch, lipophile and water by rapidly stirring together the components of the mixture at or near room temperature. When the stirrer is stopped, these mixtures tend to separate rapidly into an upper lipophilic phase and a lower phase that consists essentially of starch granules and water. The pH of the dispersion is typically in the 5–7 range, but may be optionally adjusted to any desired range by addition of acid, base or buffer system. It is well known that the properties of cooked starch are highly dependent upon the pH during cooking. As the pH is reduced to a value lower than about 4, starch will suffer increasing amounts of hydrolytic degradation, which will affect the formation and properties of the starch coating. At a sufficiently low pH, total hydrolysis of the polysaccharide occurs to yield glucose and other water-soluble sugars. The concentration of starch in water is typically about 10–15%, by weight; however, the upper limit is variable and is dictated by the desired viscosity of the cooked dispersion.

Cooking is preferably carried out with an excess steam jet cooker (see R. E. Klein and D. L. Brogly, *Pulp and Paper*, Vol. 55, pp. 98–103, May 1981) under conditions of intense turbulence and mechanical shear necessary to attain complete disruption of starch granules and complete solution in water of both the amylose and amylopectin components of starch. These components dissolve by virtue of not only the high temperature of the jet-cooking process, but also the shear-induced cleavage and rupture of starch molecules, especially those having the highest molecular weight. This intense mechanical shear not only facilitates the total and complete solubility of starch in water, but also lowers the apparent viscosity of the starch solution, as compared to either thermal steam jet cooking or conventional batch cooking. We believe that the spontaneous formation of starch coatings or shells around the individual lipophilic droplets is due to the fact that (1) starch is rendered totally soluble and is reduced in molecular weight by the cooking process and (2) the intense mixing and turbulence that takes place at the high temperatures and pressures of the cooking process converts the oil component into micron-sized droplets that become intimately mixed with starch solution. The exact mechanism by which a stable starch coating forms around each lipophilic droplet is unknown at the present time. No emulsifying or dispersing agents are used in the preparative process. Starch coatings are not formed during the high preparative mixing process. Rather, these coatings form spontaneously around each lipophilic droplet during the high temperature high shear cooking or blending step; and they remain intimately associated with the droplets when they are isolated, washed and purified.

Although jet cooking conditions may be widely varied by one skilled in the art, conditions are typically those cited in U.S. Pat. No. 5,676,994. Preferred cooking conditions are in the range 130°–150° C. (20–50 psig) within the hydroheater portion of the cooker, with a steam line pressure of 65–70 psig entering the cooker. Steam pressure as the hot dispersion leaves the cooker results in an immediate temperature drop in the cooked dispersion to 100° C.

Dispersions produced by this cooking process will contain droplets of lipophilic material with diameters ranging from less than 1 micron to about 30 microns. Typically, about 95% of these droplets will be under 10 microns in diameter. For purposes of this invention, droplets in this size range will be considered as being "micron-size". Droplet size can be controlled by varying the steam pressure and temperature used in the jet cooking process. For example, higher mechanical shear within the hydroheater, and thus a smaller average droplet size, can be achieved by increasing the steam line pressure entering the cooker. This increases the amount of excess steam passing through the hydroheater and thus increases the intensity of mixing during the jet cooking process. Subjecting cooked dispersions to repeated passes through the steam jet cooker will also decrease the average droplet size. Droplets are stabilized by the formation of extremely thin layers of starch that surround, or coat, each lipophilic droplet.

Various techniques may be used to isolate starch-coated lipophilic droplets from jet cooked dispersions. In one such technique (which will be referred to as "hot-dilution"), the hot, jet cooked dispersion is diluted immediately after cooking with several volumes of hot (95°–100° C.) water, and the diluted dispersion is then allowed to cool to room temperature. In another isolation technique (referred to as "cold-dilution"), the hot, jet cooked dispersion is first allowed to cool to room temperature, and the cooled dispersion is then diluted with several volumes of unheated water. In still another isolation technique, the hot, jet cooked dispersion is dried (for example, by drum drying), and the dried solid is then redispersed in water. It was particularly surprising to discover that the starch coatings around the droplets withstood the severity of treatment imparted by the hot dilution and drum drying. The amount of water used for dilution or redispersion should be sufficient to reduce the viscosity of the dispersion to a point whereby the spheres attain sufficient mobility in the dispersion to be readily isolated from starch that is not organized into spherical structures. Typically, the starch/lipophile dispersion is diluted with water about 15-fold to 25-fold. Diluted dispersions are then either centrifuged or allowed to stand for several hours. A layer comprised of starch-coated lipophilic droplets rises to the surface of the dispersion, because of the lower density of the starch-coated droplets relative to water; and this layer is then separated from the rest of the dispersion. In addition to the low-density fraction that rises to the surface, a high density fraction is often observed at the bottom of the dispersion. Although this fraction may be comprised largely of retrograded starch, it can also contain starch-coated lipophilic droplets. The factor that determines whether starch-coated droplets rise to the surface or settle to the bottom under the force of gravity is their cumulative density, which is governed by the weight ratio of lipophile-to-starch. For example, thin starch coatings (thin-walled spheres) on relatively large, low density lipophilic droplets yield coated droplets that rise to the surface; because they have a cumulative density lower than that of water. Conversely, thick starch coatings (thick-walled spheres) on relatively small droplets yield high-density droplets that settle on standing. Specific starch/lipophile ratios can be selected by adjusting the density of the aqueous phase such that both bouyant and sedimented combinations are excluded from the middle phase containing coated droplets of desired lipophile to starch ratio.

The thickness of the starch coating, and thus the cumulative density of coated lipophilic droplets, are influenced by several factors, some of which are: (1) The method used to isolate coated droplets, i.e., whether the jet cooked dispersion is subjected to hot-dilution, cold dilution, or drying followed by redispersion in water. Cold-dilution tends to produce a thicker starch coating; because starch is still at a high concentration when the cooked dispersion is cooled. Hydrogen-bonding and retrogradation therefore take place rapidly to form a rigid gel that is not easily dispersed or dissolved when the cooled dispersion is diluted. In the hot-dilution process, dissolved starch is diluted with hot water before gelling takes place, and a thin starch coating is therefore produced. (2) The ratio of amylose to amylopectin. Amylose solutions form gels more rapidly and at higher temperatures than amylopectin solutions and also produce gels that are more rigid. Amylose-containing starch will thus surround the lipophilic droplets with a thicker, more rigid and more water-insoluble gel coating. (3) The intensity of mixing during the dilution process. High-speed, high-shear mixing can strip away and disperse more of the surrounding gelled starch layer, thus producing a thinner starch coating. Typically, these starch layers have a thickness of less than one micron, and are often on the order of 0.1 micron in thickness. For most applications, the thickness of the shell wall should not exceed about 25% of the shell diameter.

After separation from the main body of the dispersion, the resulting free-flowing, non-coalesced, starch-coated lipophilic droplets may be freed of excess starch by water washing. The starch coating is not removed by the washing procedure. The starch coating that surrounds each lipophilic droplet prevents individual droplets from adhering to each other and coalescing, even under the high gravitational fields provided by a high-speed centrifuge. Moreover, the starch coating allows a concentrated dispersion of separated lipophilic droplets to be redispersed in water with only minimal agitation.

The starch coating is in the form of a continuous layer or shell that surrounds each lipophilic droplet. These starch coatings may be seen by: (1) Adding iodine/KI solution to an aqueous dispersion of coated droplets. This treatment causes the starch coating to assume the blue color characteristic of the amylose/iodine complex. Iodine-stained starch coatings may then be seen with a light microscope. (2) Dehydrating a concentrated aqueous dispersion of starch-coated droplets by freeze drying on a glass microscope slide. This treatment yields an oily residue. When this residue is diluted with a drop of the same lipophile used in the original preparation, the starch coatings appear as spherical shells when viewed with a phase-contrast light microscope. (3) Adding a water dispersion of coated droplets to ethanol. This treatment dissolves the lipophilic moiety and also causes dehydration of the starch coating. The resulting starch coatings or shells may then be observed in ethanol dispersion with a light microscope. (4) Using supercritical carbon dioxide to critical-point dry an ethanolic dispersion of the starch coatings or shells. This critical-point drying technique minimizes distortion of the starch moiety, and the coatings or shells may then be examined with a scanning electron microscope.

Figure 3:
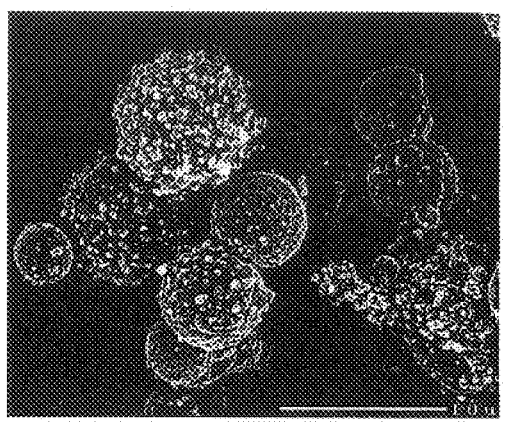
FIG. 3 is a SEM of intact starch shells isolated from the same product described in FIG. 1 after it was drum dried and redispersed in water.
Figure 2:
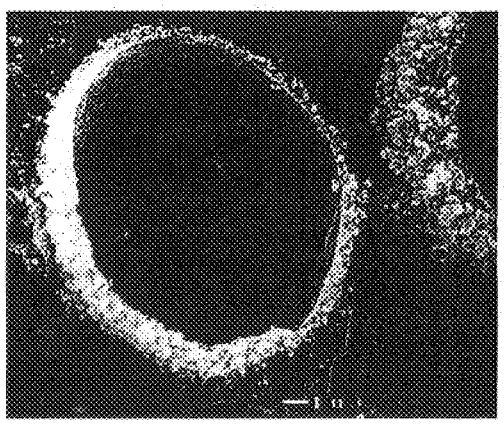
FIG. 2 is a SEM showing a fractured starch shell isolated from the same product described in FIG. 1. The SEM reveals the smooth inner surface in contrast with the rough outer surface.
Figure 4:
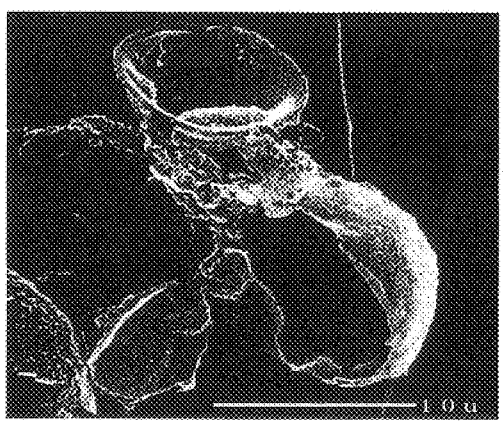
FIG. 4 is a SEM of fractured starch shells isolated from a product obtained by steam jet cooking waxy cornstarch (having an amylose content of essentially 0%) with soybean oil in a starch-to-soybean oil weight ratio of 100:40. Coated droplets (shells) were isolated by the "old-dilution" technique.

The size, shape, thickness and texture of starch coatings or shells are best seen from scanning electron micrographs (SEM's) of critical point dried samples, i.e. technique No. 4, above. FIG. 1 shows the starch coating obtained by steam jet cooking normal food grade cornstarch (having an amylose content of about 25%) with soybean oil, in a starch-to-soybean oil weight ratio of 100:40. Coated droplets were isolated from the surface of the dispersion using the hot-dilution technique. FIG. 2 shows a fragmented starch shell obtained by this method. Very similar shells (not shown) were obtained when similarly-produced product was isolated by the cold-dilution technique. FIG. 3 shows the starch coating obtained when the formulation is drum dried and the dried product is then redispersing in water. FIG. 4 shows fragments of starch shells obtained when waxy cornstarch (containing 0% amylose) is used instead of normal food grade cornstarch. This sample was isolated by cold dilution. Intact shells (not shown) were also obtained from waxy cornstarch. SEMs (not shown) also revealed the production of starch shells when normal, food grade cornstarch is jet cooked, and the hot starch solution is then blended in a separate step with soybean oil (weight ratio, 100:38.4) under high-speed, high-shear conditions. The formation of starch coatings under these conditions shows that it is not necessary to jet cook the starch and oil components together to obtain the compositions of this invention provided that blending of the components takes place prior to substantial retrogradation of the starch occurring. Starch coatings or shells are typically about 10 microns in diameter, and have a thickness of less than 1 micron. Light micrographs (not shown) of the isolated droplets stained with iodine/KI and phase contrast light micrographs of freeze-dried sample diluted with excess soybean oil confirmed that the coating is comprised of, and most likely consists essentially of, starch. Infrared spectroscopy was also used to confirm the starch structure.

By virtue of the shells consisting essentially of starch, they are considered to be both digestible and biodegradable. By "digestible" it is meant that the shells or coatings can be broken down in the digestive systems of mammals or other organisms that produce amylases in the digestive tract. By "biodegradable" it is meant that the shells or coatings are metabolized in the target organism or are readily broken down to harmless byproducts by microorganisms prevalent in the environment.

The coatings or shells of starch that surround these lipophilic droplets cause them to disperse instantly in water with gentle agitation, and the microscopic size of the droplets makes them suitable for numerous practical applications.

One such application is as a delivery system for drugs and pharmaceuticals, primarily by means of injection. Many drugs and pharmaceuticals are lipophilic in nature and can be combined with starch according to the process of this invention to yield starch-coated droplets. High-melting drugs and pharmaceuticals may be first dissolved in non-toxic, liquid oils, for example, vegetable oil or Vitamin E.

If a drug or pharmaceutical is dissolved or dispersed within the lipophilic component of these polysaccharide-coated droplets, the surrounding polysaccharide coating or shell can be used to target these drug-containing droplets and thus deliver the drug to specific sites within the body. An example of this technique is the targeting and delivery of drugs used for chemotherapy to specific tumor sites. Since targeting is known to be directed by the chemical structure of sugar units surrounding or chemically attached to the drug, the products of this invention are especially useful for drug targeting, since the structure of the polysaccharide coating or shell can be easily altered as previously described by: (1) replacing or blending starch with other polysaccharides (e.g., dextran or a galactomannan such as guar or locust bean gum) or (2) reacting sugars, such as mannose, with the polysaccharide coating or shell. The use of dextrans as drug carriers has been reviewed (L. Molteni, in *Drug Carriers in Biology and Medicine*, G. Gregoriadis, ed., Academic Press, New York, 1979, pp 107–125). The starch coating can also serve as a reactive site for the attachment of targeting proteins that can direct a bioactive agent to specific areas within the body. The term "bioactive agent" is used herein to refer to any compound or agent that would have a physiological effect on a living organism.

The coated droplets of the invention may be stored in aqueous suspension, or alternatively as a dry product that is suspended in a pharmaceutically acceptable vehicle or carrier immediately prior to administration. The terms "administer", "administration" and the like are used herein in reference to any form of parenteral introduction, such as by intravenous, subcutaneous or intramuscular injection. Other therapeutic modes of administering the compositions of this invention include oral administration and application to the skin surface. The coated droplets may also be formulated with adjuvants conventional in the art for the treatment of humans and animals. Starch hydrolysis modifying agents may also be included, which are effective for increasing or decreasing the rate at which the active agent is released through the shell.

Other applications of a non-medical nature for these starch-coated lipophilic droplets will become obvious to those skilled in the art. For example, coated droplets can be used to deliver essential oils and flavoring materials in food products, and to deliver lipophilic materials and other active components in cosmetic preparations. These droplets can also be used as delivery agents for waxes and other lipophilic materials in water-based coating formulations.

In one embodiment of the invention, a volatile lipophilic material is selected as a transient carrier for an active agent that is deposited on the inner surface of the starch shells after the lipophilic material is allowed to evaporate or is drawn off under vacuum. Also, a hydrophilic agent or material can be absorbed into hollow shells remaining after evaporation of a volatile lipophile.

When desired, these starch-coated lipophilic droplets can be made to coalesce and separate from water by removing the starch coating with a starch-degrading enzyme, for example, alpha-amylase.

The following examples further illustrate the invention but should not be construed as limiting the invention, which is defined by the claims.

EXAMPLE 1

This example demonstrates the formation of starch layers or shells around lipophilic droplets, when food grade cornstarch (amylose content, about 25%) is co-jet cooked with lipid.

Encapsulation with Food Grade Cornstarch.

A mixture of 40 g of soybean oil and 1-liter of water was stirred in a Waring® blender at high speed for 30 seconds, and 110 g of pure food grade cornstarch (moisture content, about 10%) was added. The resulting stirred mixture was passed through an excess steam jet cooker (Penick & Ford, Laboratory Model), operated with about 70 psig line pressure steam. Cooking was carried out at 140° C. (285° F.) with a steam pressure of 40 psig within the hydroheater. Pumping rate of the aqueous starch-oil dispersion through the cooker was about 1-liter/min. The cooked dispersion was collected in an insulated Dewar flask to maintain its temperature as closely as possible to 100° C. The solids concentration in the cooked dispersion was 10.44%, as determined by freeze drying an accurately-weighed portion of the dispersion.

Cold-dilution Isolation.

The following procedure was used to isolate the starch-coated lipophilic droplets of this invention by the "cold-dilution" technique. A portion of the hot, jet cooked dispersion was poured into a screw-cap bottle and allowed to stand and cool overnight. Brookfield viscosity of the cooled dispersion was 500 CP (23.9° C., No. 2 spindle, 30 rpm). A 10.0 g portion of the cooled dispersion was added to 190 g of water in a beaker, and the mixture was gently stirred (magnetic stirring bar) for 2.5 hrs. The stirrer was then stopped, and the mixture was centrifuged. The low-density surface material was isolated and washed three times with water. Although this material is comprised largely of lipid, the starch coating around each droplet allows the lipophilic layer to disperse in water with minimum agitation and also allows the material to be concentrated by centrifugation without coalescence of the individual droplets.

A second fraction, having a density greater than that of water, was also recovered as a settled layer from the bottom of the container. Although this fraction was comprised largely of retrograded starch, analysis by infrared spectroscopy showed the presence of soybean oil as a minor component. This oil component probably results from formation of a relatively thick starch coating on some of the oil droplets to give particles having a cumulative density greater than that of water.

Microscopy.

Dark-colored starch coatings surrounding each droplet could be seen by light microscopy after staining the starch component with an aqueous solution of iodine/KI. When pressure was applied to a cover glass positioned over the coated droplets of soybean oil, the oil could be seen as it was being expressed out of thick, darkly-stained starch coatings. The starch coating could also be seen by phase contrast light microscopy as dark boundaries between individual oil droplets after first removing the water by freeze drying and then adding a few drops of soybean oil to the freeze-dried residue.

Scanning electron microscopy (SEM) was used to observe the structure and morphology of the starch coatings or shells. Samples were prepared for SEM by first adding an aqueous suspension of starch-coated lipid droplets to excess ethanol to dehydrate the starch coating and to dissolve the oil component. Ethanol was then removed from the solid residue by critical-point drying with supercritical carbon dioxide. SEM of the critical-point dried solid (FIG. 1) clearly showed the starch shells that surround the individual lipophilic droplets.

Hot-dilution Isolation.

The following procedure was used to isolate the starch-coated lipophilic droplets of this invention by the "hot-dilution" technique. A 20.1 g portion of the hot, jet cooked dispersion was added to 380 g of hot (100° C.) water. The diluted dispersion was gently mixed and allowed to stand and cool overnight. Over a 12–24 hr period, the dispersion separated to yield a milky surface layer. No solid settled to the bottom of the container. The surface layer was separated, washed with water, added to excess ethanol and critical-point dried in a manner similar to that used above for the cold-diluted sample. SEM of this critical-point dried material (FIG. 2) clearly showed the starch shells that surround the individual lipophilic droplets.

Isolation by Reconstituting Drum Dried Product.

A portion of hot, jet cooked dispersion was dried on a double-drum drier heated with 40 psig steam. There was no outward separation of oil from the drum-dried product, and the dried product was not oily to the touch. A 1.5 g portion of this drum dried solid was mixed (with a spatula) with 10 ml of hot (90–100° C.) water, and this dispersion was then mixed with an additional 140 ml of hot water. The final it dispersion was centrifuged, and the surface layer was collected, washed twice with water and added to excess ethanol. Ethanol was then removed from the solid by critical-point drying. SEM of this critical-point dried material (FIG. 3) clearly showed the starch shells that surround the individual lipophilic droplets.

EXAMPLE 2

This example demonstrates the formation of starch layers or shells around lipophilic droplets, when waxy cornstarch (amylose content, 0%) is co-jet cooked with lipid.

Encapsulation with Waxy Starch.

A mixture of 40 g of soybean oil and 1-liter of water was stirred in a Waring® blender for 30 sec at high speed, and 110 g of waxy cornstarch (moisture content, about lot) was added. The resulting stirred mixture was passed through an excess steam jet cooker as described in Example 1, and the cooked dispersion was collected in a Dewar flask to maintain its temperature as closely as possible to 100° C. Solids concentration in the cooked dispersion, determined as in Example 1, was 10.46%.

A portion of the hot, jet cooked dispersion was poured into a screw-cap bottle and allowed to stand and cool overnight. Brookfield viscosity of the cooled dispersion, determined as in Example 1, was 112 CP. A 10 g portion of cooled dispersion was added to 190 g of water, and the mixture was gently stirred overnight using a magnetic stirring bar. The diluted dispersion was then centrifuged, and the upper layer of starch-coated lipid droplets was separated and water-washed. A portion of washed material was freeze-dried on a glass microscope slide, and a few drops of soybean oil was added to the oily residue. Phase contrast light microscopy showed the starch layers or shells that surround each lipophilic droplet. Another portion of washed material was added to excess ethanol. Examination of the ethanolic dispersion by light microscopy clearly showed the starch layers or shells, and collapse and distortion of these shells was also observed as the ethanol evaporated and the solvent front receded. Starch shells were isolated from the ethanolic dispersion for SEM by critical-point drying as in Example 1. The structure and morphology of these shells is shown in FIG. 4.

EXAMPLE 3

This example demonstrates the formation of starch layers or shells around lipophilic droplets when an aqueous dispersion of starch is jet cooked and the resulting hot starch solution is then blended with lipid under high-speed, high-shear conditions.

Encapsulation with Precooked Food Grade Cornstarch.

A suspension of 136 g of food grade cornstarch (same used in Example 1) in 1-liter of water was passed through an excess steam jet cooker as in Example 1, and the cooked solution was collected in a Dewar flask to maintain its temperature as closely as possible to 100° C. Solids concentration in the cooked solution, determined as in Example 1, was 9.23%. A weighed portion (405 g) of the hot starch solution was transferred to a Waring® blender bowl, and 14.35 g of soybean oil was added (this amounted to 38.4 parts of soybean oil per 100 parts dry starch, by weight). The resulting mixture was stirred at the highest speed for 2 min., and the resulting dispersion (temperature, 83° C.) was poured into a screw-cap bottle and allowed to stand and cool overnight. Brookfield viscosity of the cooled dispersion, determined as in Example 1, was 650 CP. A 10 g portion of the cooled dispersion was added to 190 g of water, and the mixture was gently stirred for about 2 hours using a magnetic stirring bar. The diluted dispersion was then centrifuged, and the upper layer of lipid-containing material was separated and water-washed. A portion of the washed lipid-containing material was added to excess ethanol, and the starch shells were isolated from the ethanolic dispersion by critical point drying as in Example 1. The structure and morphology of these shells was similar to that shown in FIGS. 1–3.

EXAMPLE 4

This example demonstrates the preparation of an aqueous dispersion of starch-coated droplets of a physiologically-active material using the process of this invention.

Encapsulation of Carbamazepine in Vitamin E/Cholesterol.

A. A solution of 11 g of carbamazepine in 200 g of alpha-tocopherol (Vitamin E) plus 20 g of cholesterol was prepared at 140–150° C. This solution was blended with a mixture of 350 g of food grade cornstarch (same used in Example 1) in 2 liters of water, and the resulting two-phase mixture was passed twice through the excess steam jet cooker under the conditions of Example 1. Examination of the cooked dispersion with a light microscope (after staining the starch moiety with $I_2/KI$) clearly showed the layer of starch that surrounds each lipophilic droplet. The hot, cooked dispersion was drum dried (drums heated with 40 psig steam); and 0.5 g of the flake-like product was redispersed in 50 ml of hot (90–100° C.) water by gently stirring with a spatula. A layer of starch-coated lipophilic droplets rose to the surface after overnight standing; and this layer was separated, washed three times with water, mixed with excess ethanol and critical-point dried as in Example 1. Examination of the critical-point dried solid by SEM showed starch shells similar in appearance to those observed in previous examples.

B. A solution of 10 g of carbamazepine in 100 g of alpha-tocopherol and 10 g of cholesterol was prepared at 150° C. A dispersion of 240 g of food grade cornstarch in 1-liter of water was jet cooked under the conditions of Example 1. The above carbamazepine solution was blended into the jet cooked starch solution, and the resulting dispersion was passed through the jet cooker a second time. The resulting dispersion was then drum dried. A dispersion of 10 g of drum dried flakes in 200 ml of hot water was stirred at high speed and was then diluted with water to 500 ml. The starch-coated lipophilic droplets that were less dense than water were then separated and washed. The carbamazepine concentration in this lipophilic fraction was 1.35%, as determined by high-pressure liquid chromatography (HPLC).

EXAMPLE 5

This example demonstrates the preparation of an aqueous dispersion of starch-coated paraffin wax droplets using the process of this invention.
Encapsulation of Paraffin Wax in Food Grade Cornstarch.

A dispersion of pure food grade cornstarch (same used in Example 1) in 2-liters of water was passed through an excess steam jet cooker as in Example 1, and 240 g of melted paraffin wax (Astorwax® 2818H; melting point, about 52–53° C.) was blended into the cooked starch solution. The resulting dispersion was then passed a second time through the jet cooker. A 150 g portion of this hot, cooked dispersion was weighed into a beaker, allowed to stand and cool for about 2 hrs and diluted with 1350 g of water. This diluted dispersion was then allowed to stand for about 1 week at room temperature. A portion of the low-density layer that had risen to the surface was separated, diluted with an equal weight of water and then added to excess ethanol. Ethanol was replaced with hexane to dissolve the paraffin wax, hexane was replaced once again with ethanol and the extracted material was critical-point dried as in Example 1. Examination of the critical-point dried solid by SEM showed starch shells similar in appearance to those observed in previous examples.

EXAMPLE 6

This example demonstrates the preparation of starch-coated mineral oil droplets using the process of this invention.
Encapsulation of Mineral Oil.

A dispersion of 110 g of pure food grade cornstarch and 40 g of pure light white mineral oil in 1-liter of water was passed through an excess steam jet cooker as in Example 1. The resulting jet cooked dispersion was smooth and creamy and showed no separation of the oil phase. When allowed to air-dry, the dispersion formed a continuous film and showed no separation of the oil phase. Hot dilution and cold dilution of the jet cooked dispersion yielded starch-coated oil droplets, and the starch coating could be seen using the critical point drying technique outlined in Example 1.

EXAMPLE 7

This example demonstrates the formation of starch layers or shells around lipophilic droplets, when high molecular weight dextran is co-jet cooked with lipid.

A mixture of 40 g of soybean oil and 1-liter of water was stirred in a Waring® blender for 30 sec at high speed, and 114.2 g of dextran (molecular weight $5-40 \times 10^6$, moisture content, 12.2%) was added. The resulting stirred mixture was passed through an excess steam jet cooker and collected as in Example 1. Solids content in the cooked dispersion, determined as in Example 1, was 10.66%. Hot dilution and cold dilution of the jet cooked dispersion, using procedures outlined in Example 1, yielded dextran-coated oil droplets. Dextran coatings were isolated and observed by SEM using the critical point drying technique outlined in Example 1. These coatings or shells were similar in appearance to the starch shells observed in previous examples.

We claim:

1. A composition consisting of discrete spherical shell and optionally material encased in said shell selected from the group consisting of lipophilic material and bioactive material, wherein the structural component of said shell consists essentially of non-cross-linked jet-cooked starch.

2. The composition of claim 1, wherein said jet-cooked starch is corn starch.

3. The composition of claim 1, wherein said shell is in aqueous dispersion.

4. The composition of claim 1, wherein said shell has a thickness of less than 25% of the shell diameter.

5. The composition of claim 1, wherein said lipophilic material is encased in said shell.

6. The composition of claim 5, wherein said lipophilic material is selected from the group consisting of lipids, fats and oils.

7. The composition of claim 5, wherein said lipophilic material is a bioactive material.

8. The composition of claim 5, wherein said lipophilic material is a carrier for a bioactive material.

9. The composition of claim 1, wherein said bioactive material encased in said shell.

10. The composition of claim 9, wherein said bioactive material is deposited on the inner surface of said shell.

11. The composition of claim 1, wherein said jet-cooked starch is excess steam jet-cooked starch.

12. The composition of claim 1, wherein said jet-cooked starch has a reduced molecular weight compared to the starch prior to jet-cooking.

13. The composition of claim 1, wherein said jet-cooked starch is unmodified starch.

14. The composition of claim 1, wherein said jet-cooked starch has an amylose content of 25% or greater.

15. The composition of claim 1, wherein said jet-cooked starch consists essentially of amylopectin.

16. The composition of claim 1, wherein said shell has an inside diameter of 1–30 microns and a thickness of less than one micron.

17. The composition of claim 1, wherein said jet-cooked starch is a drum-dried jet-cooked starch.

18. The composition of claim 1, wherein said jet-cooked starch shell has a protein attached thereto.

19. The composition of claim 9, wherein said bioactive material is a drug or pharmaceutical.

* * * * *